(12) United States Patent
Miglio et al.

(10) Patent No.: US 9,593,067 B2
(45) Date of Patent: Mar. 14, 2017

(54) METHOD FOR RECOVERING INTRACELLULAR COMPONENTS FROM FERMENTED MICROORGANISMS

(71) Applicant: ENI S.p.A., Rome (IT)

(72) Inventors: Roberta Miglio, Oleggio (IT); Alfredo Montini, Segrate (IT)

(73) Assignee: ENI S.p.A., Rome (IT)

( * ) Notice: Subject to any disclaimer, the term of this patent is extended or adjusted under 35 U.S.C. 154(b) by 46 days.

(21) Appl. No.: 14/442,840

(22) PCT Filed: Dec. 11, 2013

(86) PCT No.: PCT/IB2013/060813
§ 371 (c)(1),
(2) Date: May 14, 2015

(87) PCT Pub. No.: WO2014/097057
PCT Pub. Date: Jun. 26, 2014

(65) Prior Publication Data
US 2015/0299096 A1  Oct. 22, 2015

(30) Foreign Application Priority Data
Dec. 20, 2012  (IT) .............................. MI2012A2195

(51) Int. Cl.
C12P 7/64 (2006.01)
C07C 67/48 (2006.01)
C12N 1/06 (2006.01)

(52) U.S. Cl.
CPC .............. *C07C 67/48* (2013.01); *C12N 1/066* (2013.01); *C12P 7/6463* (2013.01)

(58) Field of Classification Search
CPC .............................. C07C 67/58; C12P 7/6463
See application file for complete search history.

(56) References Cited

U.S. PATENT DOCUMENTS

2011/0183403 A1* 7/2011 Dierkes .................... C11B 1/06
435/257.1

FOREIGN PATENT DOCUMENTS

WO    WO 2010/015398 A1    2/2010

OTHER PUBLICATIONS

International Search Report issued Mar. 24, 2014 in PCT/IB2013/060813.
Cunwen Wang, et al., "Technologies for extracting lipids from oleaginous microorganisms for biodiesel production" Frontiers in Energy, vol. 6, No. 3, XP035111647, 2012, pp. 266-274.

* cited by examiner

*Primary Examiner* — Rosanne Kosson
(74) *Attorney, Agent, or Firm* — Oblon, McClelland, Maier & Neustadt, L.L.P.

(57) ABSTRACT

The present invention relates to a method for the recovery of intracellular components of materials of a biological origin, such as yeasts, algae, bacteria and/or mildews, after fermentation/cultivation, which comprises a thermal lysing treatment via nebulization and the use of a nebulization solvent capable of extracting said intracellular components once the nebulization has been completed.

20 Claims, 7 Drawing Sheets

Fig. 6

| Stream | 1 | 12 | 13 | 15 | 2 | 4 |
|---|---|---|---|---|---|---|
| Vapour fraction | 0.0 | 0.0 | 0.0 | 0.1 | 1.0 | 0.0 |
| Temperature °C | 40.0 | 35.0 | 190.0 | 61.8 | 233.8 | 150.0 |
| Pressure [bar] | 1.00 | 20.00 | 20.00 | 1.00 | 30.00 | 1.00 |
| Massive flow-rate [kg/h] | 1.0 | 0.7 | 0.7 | 1.7 | 0.3 | 0.3 |
| Volumetric flow-rate [m3/h] | 1.01 | 0.99 | 0.99 | 2.00 | 1.37 | 0.31 |
| Heat Flow [kcal/h] | -6.65E+03 | -3.91E+02 | -3.24E+02 | -6.98E+03 | -4.29E+03 | -8.60E+01 |
| Solid weight fraction | 10.2% | | | 6.2% | | 34.6% |
| Density [kg/m3] | 1104.3 | 650.6 | 460.8 | 11.9 | 12.8 | 976.1 |
| Weight fractions | | | | | | |
| Water | 0.6915 | 0.0008 | 0.0008 | 0.4183 | 1.0000 | 0.0001 |
| Sugars | 0.0027 | 0.0000 | 0.0000 | 0.0016 | 0.0000 | 0.0092 |
| n-hexane | 0.0000 | 0.9981 | 0.9981 | 0.3948 | 0.0000 | 0.0006 |
| Rhodotorula | 0.0000 | 0.0000 | 0.0000 | 0.0000 | 0.0000 | 0.0000 |
| Cellular residues | 0.0000 | 0.0000 | 0.0000 | 0.0618 | 0.0000 | 0.3465 |
| Lipids | 0.0000 | 0.0000 | 0.0000 | 0.1196 | 0.0000 | 0.6433 |
| Other products | 0.3058 | 0.0010 | 0.0010 | 0.0038 | 0.0000 | 0.0003 | table 4

Fig. 6 (continuation)

| Stream | 3 | 5 | 8 | 6 | 11 | 7 | 10 | 9 |
|---|---|---|---|---|---|---|---|---|
| frazione vapore | 1.0 | 0.2 | 0.0 | 0.0 | 0.0 | 0.0 | 0.0 | 0.0 |
| Temperature °C | 150.0 | 80.0 | 32.2 | 90.5 | 33.7 | 32.2 | 20.0 | 32.0 |
| Pressure [bar] | 1.00 | 1.00 | 0.90 | 1.00 | 20.00 | 0.90 | 1.00 | 0.90 |
| Massive flow-rate [kg/h] | 1.6 | 1.6 | 0.6 | 0.9 | 0.7 | 0.0 | 0.0 | 0.7 |
| Volumetric flow-rate [m3/h] | 1.95 | 1.95 | 0.98 | 0.94 | 0.99 | 0.04 | 0.01 | 0.99 |
| Heat Flow [kcal/h] | -7.22E+03 | -7.74E+03 | -3.88E+02 | -7.17E+03 | -3.91E+02 | -3.04E+02 | -4.22E+00 | -3.92E+02 |
| Solid weight fraction | 0.0% | | | | | | | |
| Density [kg/m3] | 0.8 | 3.9 | 651.0 | 952.4 | 651.8 | 991.4 | 661.7 | 651.1 |
| Weight fractions | | | | | | 0 | 0 | 0 |
| Water | 0.5875 | 0.5875 | 0.0008 | 0.9788 | 0.0008 | 0.9662 | 0.0000 | 0.0008 |
| Sugars | 0.0000 | 0.0000 | 0.0000 | 0.0000 | 0.0000 | 0.0000 | 0.0000 | 0.0000 |
| n-hexane | 0.4038 | 0.4038 | 0.9981 | 0.0070 | 0.9981 | 0.0288 | 1.0000 | 0.9981 |
| Rhodotorula | 0.0000 | 0.0000 | 0.0000 | 0.0000 | 0.0000 | 0.0000 | 0.0000 | 0.0000 |
| Cellular residues | 0.0000 | 0.0000 | 0.0000 | 0.0000 | 0.0000 | 0.0000 | 0.0000 | 0.0000 |
| Lipids | 0.0049 | 0.0049 | 0.0000 | 0.0084 | 0.0000 | 0.0000 | 0.0000 | 0.0000 |
| Other products | 0.0038 | 0.0038 | 0.0011 | 0.0057 | 0.0011 | 0.0050 | 0.0000 | 0.0011 | table 4

METHOD FOR RECOVERING INTRACELLULAR COMPONENTS FROM FERMENTED MICROORGANISMS

BACKGROUND OF THE INVENTION

The present invention relates to a method for recovering intracellular components of materials of a biological origin, such as yeasts, algae, bacteria and/or mildews.

It is known in the art that suspensions of cellular microorganisms can be lysed by perturbation and breakage of the cell membrane for example by variations in the osmotic pressure. The simple lowering of the ionic force of the liquid environment, for example, or the addition of a surfactant with moderate stirring of the suspension, allows the cells to be swollen and allowing them to be lysed. In other cases, on the other hand, a vigorous stirring of the suspension is necessary, together with a strong thermal, mechanical or sonic action for disrupting the cell membranes, with an increase in the costs of the cell lysis. The cells of bacteria, yeasts and algae, for example, are much more resistant and their lysis for recovering the intracellular components is difficult so that resort must be made to more effective methods than osmosis for obtaining them.

In "Disruption of microbial cells for intracellular products", Enzim Microb Tech., 1986, vol. 8, the main methods are outlined for the disruption of the cell wall, which are:
a) Mechanical methods:
  by means of frictional forces between cells and solid material, for example with bead mills or X-presses or Hughes presses;
  by means of frictional forces in a suspension of cells, for example with ultrasounds or with high-pressure homogenizers or with so-called French-presses.
b) Non-mechanical methods:
  by means of enzymatic, chemical lysis (with detergents, solvents or antibiotics) or physical lysis (osmotic shock or pressure).

In industrial processes which, at the end of the fermentation, provide for the collection of micro-organisms and their cell breakage or lysis in order to release the intracellular product, an oily and aqueous enzymatic phase often accompanies the residues of the cell.

An approach to the extraction of oils from seeds followed by industry is the use of process units (malaxation) having an adequate volume stirred by helicoidal blades which rotate at a rate of 20-30 rpm and guarantee an adequate residence time (1-2 or more hours) for the disruption process for releasing the oily vacuoles. This process is carried out at a low temperature (20-30° C.) in air.

An industrial plant can generally comprise more kneaders arranged in series (in this case often superimposed in order to limit the encumbrance space) or in parallel, mechanically charged, by means of a hydraulic system, with the oil paste leaving the crusher. This process produces a bland thermal lysis which, associated with a slow remixing of the paste, allows the oily phase to be released, which is then separated by floatation process. This technology is effective for microorganisms having dimensions larger than a few tens of microns, but it is not effective for resistant micro-organisms such as some, but not only, of the *Lypomyces, Rhodotorula* and *Cryptococcus* species. The technical parameters indicated for this process are the temperature and duration of the operation. The temperature is fundamental for the yield in the subsequent extraction and is strictly associated with the releasing phase of the cell content. The time parameter is correlated with the operative mode.

Another type of industrial machine capable of effecting this process for cases of cell lysis which require drastic temperature and pressure conditions, is a machine consisting of a fixed or rotating cylinder, equipped with internal blades or mixers capable of mixing, breaking and accompanying the cells to be lysed. This machine is used in the food industry for thermal hydrolysis and, at times in acid environments for sulfuric acids (see for example Anco-Eaglin Inc machines).

American patent application US 2010/0006515 A1 describes a machine for thermomechanical cell lysis which acts as a screw press for pressures greater than bar and temperatures higher than 120° C. In the description, it is indicated that this machine can also carry out a separation of the cellular liquids during the thermal lysing process for cellular products with membranes characterized by a strong thermal/mechanical breaking strength.

The use of glass or ceramic ball mills allows a vigorous shaking and breakage of the cells in the paste to be lysed. The method has been used for years and is considered as being applicable to the biological group of yeasts and fungi, microbacteria, spores and micro-algae. It has more recently been applied to samples of soil and small samples of vegetables and animal tissue.

Although both methods, those based on mills and on screw drums, are effective for certain types of cells, they are characterized by a high operating cost and also cost of the equipment. The latter derives from the times necessary for effecting the lysing action and, at times, due to the chemical aggressiveness of the growth environments which accompany the cellular micro-organisms, as in the case of algae, where the presence of chlorine requires the use of highly resistant materials such as alloys mainly based on nickel and chromium.

More recently, methods based on sonic or magnetic lysis processes have been used, which imply a lower final energy cost.

The intense sonication of liquids, for example, generates sound waves which propagate in liquid mediums with alternating high- and low-pressure cycles. During the low pressure cycle, a high intensity of small-sized vacuum bubbles is created in the liquid. A cavitation process is therefore used for the implosion of the liquid bubbles, which thus allows shear forces to be generated which are capable of mechanically breaking the cell structure. This effect is used for the extraction of lipids from algae. In order for the separation of the oily/lipid phase from the aqueous phase and cell debris to be effective, the addition of a solvent is required, as otherwise the cell debris would also remain englobed in the oily/lipid phase.

Other methods comprise the crushing of cells by means of high-pressure passage (20,000-30,000 psi or 140-210 MPa) through a valve having a narrow orifice. The fluid is therefore subjected to high shear forces with a consequent breakage of the cells. The shear force for optimizing the breakage of the cell is defined by controlling the pressure. The system requires high energies and a cooling for samples that require multiple steps through the system.

Mechanical homogenization is included in these mechanical methods, which operates under high-pressure conditions and with the use of a high energy density which is based on the use of pressure and microvalves for dividing the particles until they have been reduced to minimum dimensions (below a micron). The homogenizing valves are dimensioned for obtaining the desired micronization and dispersion degree at the lowest possible pressure, depending on the various applications. They are continuous industrial machines which can also manage voluminous flow-rates with low specific energies of use (for example, a machine which handles liquid flow-rates of 6 m³/h, with overpressures of 1,500 bar, requires a power equal to 315 kW).

Another approach for thermal lysis is described in literature under the name of "Hydrothermal treatment" which is experimentally applied for the lysis of algae, and is proposed for the extraction of lipids contained in oily seeds. The process is provided with experimental data for the release of the lipids contained in algae. The operation consists of a thermal lysis mechanism on a liquid-solid suspension under pressure (200 atm) and at a temperature ranging from 250 to 300° C. The final extraction of the lipids from the solid lysed cell mass, is carried out with n-hexane. The technological approach to the problem developed by this latter technology, as also those using pressurized homogenization systems, require costly industrial applications, above all for the materials used which must guarantee due resistance to the physico-chemical system composed of the suspension to be treated under the conditions of the lysing method ("Hydrothermal processing of high-lipid biomass to fuels" Johnson, Michael C., Ph. D. Massachusetts Institute of Technology. Dept. of Chemical Engineering Massachusetts Institute of Technology Issue Date: 2012).

International patent application WO 99/15638 relates to a method for modifying the structure of lipid membranes such as double lipid layers of micro-organisms, eukaryotes or prokaryotes, liposomes, vesicles or living cells. In particular, this method creates an instability (perturbation) of the lipid structure which allows the fusion of the lipid membranes without lysing the cells involved.

The method described in WO 99/15638 provides for the use of a low-temperature spray dryer) for atomizing into small drops a liquid medium such as, for example, a physiological solution, milk, blood, serum, fermentation broths and water, containing the lipid structure, which are introduced at high velocity into an environment containing vapour at a controlled temperature.

In the method of WO 99/15638, the liquid medium used for suspending the cells or lipid structures to be fused during the nebulisation, favours the fusion process of the cell membranes by lysis on the part of these. The liquid medium used must consequently not favour the breakage of these membranes but their aggregation. The objective of the process of WO 99/15638 is not to destroy the membranes of two or more different cell entities, but to keep the characteristics of the original cells unaltered, thus allowing a partial fusion of the cell membranes. In this way, the method produces molecular aggregates which combine the characteristics of the aggregated cells in the multicellular mixture.

In the lysis of a cell, one wants to recover the product of the process from micro-organisms subjected to fermentation or cultivation, and a lysing or breakage must firstly be effected, for example thermally, in a process volume, or reactor, suitable for obtaining temperatures higher than 120° C., at a pressure of at least 5 bar, for a time ranging from 10 minutes to 4-5 hours under moderate stirring, i.e. the conditions necessary for the lysis of the micro-organisms. It is subsequently, necessary to: start the reactor cooling; to extract the mass from the reactor as a suspension of solid residues, oils, water and other intracellular products; and finally an organic, or inorganic solvent must be added, or mixtures thereof, in order to obtain, with subsequent operations of solubilisation and separation of the liquids from the solids, the cell content produced of the fermentation or cultivation process.

This method is characterized in that over 90% of the energy requirements of the overall extraction process of the product of the fermentation process is due to the thermal lysis effected on the fermented micro-organisms.

SUMMARY OF THE INVENTION

It is therefore of great interest to find a new method for obtaining intracellular components of fermented biological materials, in which the energy requirements of the overall method are much fewer than those of conventional processes.

The present invention relates to a thermal lysing method for the recovery (extraction) of intracellular components of materials of a biological origin, such as cultivated yeasts, algae, bacteria and/or mildews, or in particular, fermented products, which allows the operating costs and costs of the equipment used in the lysing process of said bio-industrial processes, to be minimized.

The method of the invention comprises:
  co-feeding at least two streams to a nebulizer, wherein the first stream comprises the aqueous suspension of cellular microorganisms to be lysed and the second stream comprises a liquid or gaseous solvent (nebulization solvent);
  nebulization of the suspension containing said microorganisms and their thermal cell lysis in an environment characterized by a high exchange surface and therefore characterized by a low contact time in a small treatment volume or reactor, which normally leads to a relatively lower cost of the equipment;
  separating the intracellular components from the cell residues deriving from the lysis.

DETAILED DESCRIPTION OF THE INVENTION

The liquid which accompanies the cells in the suspension, or nebulization solvent, is normally water and/or another chemical compound which favours the laceration process of the cell membranes to release the contents of the cell. The solvent used must therefore favour the breakage of these membranes and also favour the separation of the intracellular products from the remaining solid matrix. Specific examples of nebulization solvents are organic solutions, such as for example hydrocarbons, alcohols, esters, ethers. When the nebulization solvent is a liquid aqueous solution, inorganic acids can also be added to the same.

The nebulization of the suspension of microorganisms takes place in an expansion chamber (nebulization chamber or thermal lysing unit) containing an inert gas, water vapour, carbon dioxide and/or an organic solvent in gaseous phase, at high temperatures. The nebulization chamber can already be at the lysing temperature, i.e. ranging from 90° C. to 180° C., preferably from 120° C. to 160° C. and even more preferably from 130° C. to 150° C.

The advantage of the present invention is, in fact, that it is possible to operate at lower temperatures with respect to those normally used in the lysing processes known in the art.

The interaction with a high contact surface, created thanks to the nebulization, allows a rapid transfer of kinetic energy to the nebulized suspension which causes the mechanical breakage of the cell wall and/or cell membranes of the microorganisms present in the nebulized drops, by expansion. The release of the intracellular contents produced by cultivation or in particular by fermentation is thus obtained, which can then be recovered along the process units following the thermal lysing unit.

Subsequent process units are present after the first nebulization chamber, such as, for example, accumulation tanks, cyclones or surface condensers which are kept at a progressively decreasing temperature and along which the separation of a multiphase suspension is observed, composed of the intracellular contents, solids (cell debris), an aqueous and oily liquid due to the condensation of part of the atmospheric vapours of the nebulization chamber, the latter due to the solvents which are co-fed together with the suspension of cells, and intracellular contents or lipids.

The aqueous phase contains: water, residues of the cultivation or fermentation broth, salts, solvents and a few solubilized lipids. The lipid or oily phase contains: organic solvents, fatty acids, lipids, water, and their salts. The solid phase comprises the solid residues remaining from the cell aggregates (cell debris) which may still contain non-extracted lipids, and which can be optionally subjected to one or more additional lysing operations by subsequent nebulization operations and completion lysis in the same equipment, by recycling together with the primary feeding, to the head of the nebulization chamber, or into a subsequent lysing unit.

The multiphase suspension, produced in the nebulization chamber, is then subjected to separation gravimetrically or by centrifugation, in order to separate the water and solids from the oily phase containing the solvents and lipids. The nature of the solvent (initial nebulization solvent) used also influences this operation as it can create phases in the form of foamy suspensions which are difficult to treat. The choice of nebulization solvent must therefore also favour the separability of the components of the suspension obtained after the lysis.

A recovery step of the nebulization solvent is always present downstream of the separation step of the solid phases from the liquid phases, analogously to chemical processes of solvent extraction.

The lipids recovered can be used as such or sent to treatment destined for the final use of the same, for example within the range of use as biofuels, hydrogenation or trans-esterification treatment.

The intracellular contents of interest are separated from the solvent/aqueous phase by means of gravimetric separation or centrifugation. At the end of the separation train, the water can remain partly in vapour form and partly in condensed form. Water is always present, as it derives from the water present initially inside the cells.

In particular, the method of the invention can be used in production processes of lipids obtained as intracellular compounds in yeasts grown on sugar substrates. These cellular organisms, such as, for example, the yeasts *Lypomyces, Rhodotorula* and *Cryptococcus*, have a cellular wall which is particularly resistant also to the actions of strong mechanical/thermal stress corresponding to pressure even higher than 1000 bar.

The nebulization action reduces the energy requirements of the overall process, as the heat exchange on the basis of the lysing process is favoured by the high heat exchange surface which is formed with the nebulization and cavitation phenomena induced by the high thermal profiles through the cell.

The environment created by the nebulization is, in fact, characterized by a high energy transfer at the cell interface, as an increase in the heat exchange between the gaseous phase and liquid phase is observed. The heat exchange between gaseous phase and liquid phase is due to the fact that the interface between the two phases is greater, the smaller the diameter of the drops of liquid-solid suspension, and the transfer rate of the energy through the cell membranes increases considerably in relation to an increase in the liquid/gaseous atmosphere contact surface which is inversely proportional to the diameter of the drop and which therefore increases its efficacy by about three measurement units with respect to cases of evaporation of the liquid from a gravitational separation surface. Typical values of the coefficient of liminal convective heat exchange, h, for water and air are: $h=10\text{-}100$ $W/m^2K$; water=$500\text{-}10{,}000$ $W/m^2K$.

The solvents used for the nebulization and subsequent extraction of the intracellular components of yeasts, algae, bacteria and/or mildews are polar organic solvents, such as alcohols, esters, ketones, in particular methanol, ethanol, isopropanol and/or ethyl acetate are preferred, apolar organic solvents such as alkanes, in particular hexane and/or iso-octane are preferred, refinery cuts characterized by a normal boiling curve ranging from 50° C. to 180° C., preferably 100° C., mixtures of various organic refinery substances, such as petroleum ether, naphthas and/or alkylated gasolines, or mixtures of the above-mentioned solvents.

The nebulization chamber in which the suspension containing the microorganisms is effected, can contain an inert gas such as, for example, nitrogen, helium, argon, carbon dioxide, in addition to water vapour, or saturated or overheated vapours of the organic solvents indicated above as nebulization solvents. This enables both the lysis of the microorganism and the extraction in the solvent of the intracellular components of interest.

The extraction of the intracellular liquids from the solid matrix of the microorganism is favoured by the pressurized solvent. The extraction is then improved by a centrifugal action which favours the extraction for different densities of the solid and liquid phases of the suspension formed.

In order to obtain the thermal lysing, the temperature in the nebulization chamber is within the range of 90° C. to 180° C., preferably ranging from 120° C. to 160° C. and even more preferably from 130° C. to 150° C.

In particular, the latter range is preferred for yeasts, in particular the yeasts *Lypomyces, Rhodotorula* and *Cryptococcus*.

The mixing of the nebulization solvent with the cellular suspension before nebulization could improve the overall yield of the lysing process, as it could act chemically on the double lipid layer which forms the cell membrane, as observed in the technical solutions of the prior art. In the art, in fact, a prolonged contact time between the solvent and cells to be lysed is an important factor, together with the temperature and pressure for obtaining the lysis of the microorganisms.

This prolonged contact time, however, represents a further energy cost, whereas the present invention aims at reducing these costs and is therefore characterized by low contact residence times of the solvent with the cells to be lysed, both when the solvent is put in contact with the cells before being introduced into the nebulizer, and also when the solvent is present in the nebulization chamber where the suspension of microorganisms to which the solvent has not been previously added, has been nebulized.

The dimensioning of the nebulization volume for the method at the basis of the present invention arises from the application of the concept of separation of the suspension containing the solid-liquid phases, deriving from the cell lysing action, from the vapours released after nebulization. This concept also envisages the use, necessary at times, of various separation chambers, arranged in series with respect to the gas flow, which are necessary for favouring the separation of the cell contents in addition to the solid residues of the lysed cell.

The form of the nebulization chamber must favour the separation from the vapours of the suspension and the outflow and collection of the latter from the bottom of the same. Cylindrical forms, also sandwiched by gridded or lamellar velocity reducers, with a truncated-conical terminal for collecting the suspensions, are preferred forms of the nebulization chamber.

A situation where there is an increasing thermal profile between the first and subsequent chambers, does not influence the lysing action, when these temperatures are below the temperature and pressure values envisaged by the method. It can generally be said that higher temperatures in the chambers following the nebulization chamber can be counterproductive in terms of chemical effects on the lysed liquids.

The thermal profile, along the process line which starts from the nebulization volume, which is defined by the heat exchange effected at the wall or by means of exchange inserts in the separator volumes, generally influences, on the other hand, the release of solvents from the suspension deriving from the lysis. This profile is defined by the flow-rate of the gases released and entrainment permitted of the cell contents due to the physico-chemical liquid/vapour equilibrium and action of the gas velocities.

The nebulization chamber can already be at the lysing temperature or at higher temperatures in order to favour high treatment flow-rates in the lysis, and contains the above-mentioned gases or vapours at a temperature equal to or higher than the temperature at which the lysis and extraction are to be effected.

The suspension containing the microorganisms to be lysed can enter the nebulization chamber at a lower temperature than that at which the lysis is to be carried out. In this case, the solvent enters with a flow and thermal level which are such as to reach, together with the substance to be lysed, the lysis conditions in the nebulizer.

Part of the endo/exo cell water present and part, or all, of the solvent possibly fed with the suspension of microorganisms, evaporate in the nebulization chamber, by lowering the temperature which was present in the nebulization chamber before the suspension of microorganisms was fed, releasing high-boiling liquids such as intracellular lipids, which are separated on the walls of the chamber together with the cell debris.

A possible increase in temperature in the separation volumes, subsequent to the nebulization chamber, has a negative effect on the lipids, increasing the quota of fatty acids contained in the suspension. This increase, however, can favour the extraction from the solid matrix.

After lysing, the intracellular components of interest of a lipid nature, such as triglycerides, mono and diacyl glyceride fatty acids, phospholipids, phytols, cholesterols, are released in a suspension of high-boiling oils (lipids have a boiling point at room temperature higher than 300° C.) together with the solid cell residues. The suspension of high-boiling oils is then separated from the nebulization solvent, if this can be separated from said oils, such as, for example when the solvent is aqueous or polar, and is sent to separation of the solid cell residues (debris); as already previously pointed out, this separation can be effected gravimetrically, by density, centrifugation or filtration, for example with a hydrocyclone, decanter or tricanter or by distillation, by means of membranes or by evaporation of the product from the nebulization/extraction solvent.

The water present in the expansion chamber, of an intracellular origin or deriving from the suspension of cells or from the high-temperature vapour possibly added for purposes of heat exchange, together or separately with the suspension to be lysed, is preferably removed from the suspension to facilitate the subsequent solid/liquid separation, avoiding foams and suspensions which negatively interact on the subsequent separation of the cell products. The nebulization solvent is optionally fed together with pressurized water vapour in order to control the lysing temperature in the nebulizer. This operative methodology is used if there is an easy water/solvent separation in liquid phase. In these cases, the vapour, containing the solvent and water, is sent to a second chamber and once separated from the water, is recycled to the nebulizer, where it is integrated with fresh solvent.

The equipment which can be used for the nebulization is basically analogous to or the same as that used for the nebulization operation of a liquid suspension of a solid (spray-dryer). A spray-dryer is a combination of apparatuses composed of a feeding pump of a liquid containing a suspension, an inorganic solid or not, a gas or vapour source such as a thermal and mechanical energy carrier, an atomizer, a heater, a dispersion space of the vapour/liquid/solid mixture leaving the atomizer, or drying chamber, in addition to treatment/condensation systems of the vapour/exhaust gas mixture and recovery of possible powders. The solid compound is extracted dry at the temperature of the drying chamber.

Taking into consideration the conditions necessary for the thermal lysis of the microorganism and extraction conditions of the product from the cellular substance in which this is withheld, a series of functioning conditions can be specified for the lysis and recovery of the solid, liquid or solubilized lipid in the solvent, if this is used.

The materials to be used for lysing applications must be defined in relation to the operating conditions, i.e. in relation to the nominal functioning temperature and pressure, and in relation to the resistance to the aggressiveness conditions of the environment in turn in relation to the solvents and contents in the liquids which accompany the cells.

The application method, object of the present patent application, allows considerable savings on the variable and CAPEX costs (Capital expenditure) of the plants for effecting lysing operations of cells and extraction of the intracellular compounds, due to the fact that, thanks to the method of the invention, there is a significant energy saving, as apparatuses for thermally or mechanically lysing the cells in a first phase with subsequent costly extraction units of the lipid, are no longer necessary.

BRIEF DESCRIPTION OF THE FIGURES

in FIG. 5, the plant scheme of a closed-cycle solution is represented, for implementing the method of the invention.

FIG. 6: in FIG. 6, table 4 is illustrated, which indicates the material and energy balance of the relative example of a *Rhodotorula* treated via sugar fermentation.

EXAMPLES

Example 1

Three suspensions of yeasts in water of the type *Lypomyces, Rhodotorula* or *Cryptococcus* (biomass) were used for the recovery of the intracellular components according to the method of the invention. No other solvents were added to the suspension in the nebulization phase.

In the present example, the objective is only to define the lysing capacity of the process proposed. The effective lysis is then evaluated a posteriori with classical analyses by means of a Soxhlet liquid-solid extraction unit.

For the nebulization of the suspension, a MINI Spray Dryer 190 of the supplier BUCHI was used, which, as a dryer, was capable of evaporating about 100-500 g/h of water with a flow of $N_2$ of 700-1,000 Nl/h which can be heated to a maximum temperature of 250° C., and which is therefore capable of producing about 1-100 g/h of dried powder having a particle-size in the order of 0.2-10 microns.

The overall time used by the biomass for following the "hot part" of the circuit as far as the nebulizing nozzle, was 10-30 seconds. The whole circuit of gas fed to the nebulization chamber as far as the nebulization or spray chamber, is under a slight vacuum, indicatively 0.97 atm.

Nitrogen was present as inert gas in the nebulization chamber in which the suspension to be treated was sprayed, whose temperature was maintained at approximately the same value as that at the inlet of the cyclone separator (temperature to which the sample is immediately brought after the nozzle by evaporation of the suspension water and which was constantly monitored as indicated in Table 1).

A Soxhlet unit was used for the extraction of the lipids from the cellular solids. A paper thimble was washed with the extraction solvent and then brought to a constant weight in an oven at 105° C. The solid to be treated (3-20 g) was charged into the thimble. The extraction solvent (150-200 ml) was charged into the flask, whose tare-weight had been accurately determined. In the example cases described in Tables 1 and 2, the following products were used: hexane, characterized by a boiling point of 69° C. and a density of 0.655 g/ml, polarity index 2, ethyl acetate, characterized by a boiling point of 77° C. and a density of 0.90 g/ml, ethanol, characterized by a boiling point of 79° C. and a density of 0.789 g/ml, polarity index 24. Boilers were introduced into the flask and the flask was heated with an oil bath. The solvent was re-condensed with a water condenser in the upper part of the Soxhlet. About 10 extraction cycles were effected, at the end of the last cycle, the thimble was removed and placed in an oven at 105° C. until a constant weight was obtained.

In order to separate the extraction solvent from the lipid extract, the Soxhlet was substituted with a claisen, and the solvent was distilled, first at atmospheric pressure and then under vacuum at about 0.005 absolute atm. The lipid extract remains in the flask.

An optical microscope was used for determining the morphology of the particles before and after the nebulization operation and a thermobalance (Perkin Elmer) was used for characterizing the humidity degree and ash content of the powders obtained.

Fourier transform spectrophotometrical analyses (FT-IR) were effected for characterizing the lipid extract. The extracts were characterized by means of FT-IR analysis (Nicolet Nexus 670) within the range of 4,000-1,000 $cm^{-1}$ (at 2 $cm^{-1}$) in transmission by casting the extract as such on a tablet of $CaF_2$.

The nebulizations indicated in Table 1 below were effected using the method described above.

The test SD100 was carried out with a diluted feeding of about 1:3 in demineralized $H_2O$ with respect to the others. The three tests differ in the temperature of the nebulization chamber (T out in Table 1 below) and in particular 95°, 130° and 150° C. It should be noted that the *Cryptococcus* used for the test SD104, indicated in the table before drying in the spray dryer, was subjected to diafiltration with the addition of demineralized water and ultrafiltration to separate/collect the yeast cells and leave the sugars present initially with the yeast in water, in order to remove the residual glucose of the fermentation.

TABLE 1 nebulization conditions.

| TEST | SUSPENSION | weight (g) | dry weight (dw %) |
|---|---|---|---|
| SD100 | Lypomyces | 150 | 9.8 |
| SD101 | Lypomyces | 19 | 29.5 |
| SD102 | Lypomyces | 67 | 29.5 |
| SD103 | *Rhodotorula* | 26.8 | 13.0 |
| SD104 | *Cryptococcus* | 127.2 | 4.2 |

| TEST | SPRAY CONDITIONS nitrogen (l/h) | Vacuum atm | Set point Pump | T in (° C.) | T out (° C.) | f. weight (g) | estimate recovery (dw %) |
|---|---|---|---|---|---|---|---|
| SD100 | 550 | 0.975 | 4 | 210 | 95 | 6.9 | 47% |
| SD101 | 550 | 0.975 | 3 | 220 | 130 | 3.8 | 67% |
| SD102 | 551 | 0.975 | 4 | 250 | 150 | 16.2 | 82% |
| SD103 | 551 | 0.975 | 3 | 250 | 130 | 2.5 | 73% |
| SD104 | 500 | 0.975 | 3 | 250 | 150 | | |

Key to Table 1:

Test=test code

Weight (g)=quantity of yeast suspension nebulized

Dry weight (dw %)=quantity of yeast in the nebulized suspension

Nitrogen (l/h)=flow-rate in the hot gas fed to the nebulization chamber

Vacuum (atm)=absolute pressure of the nitrogen after the cyclone in which the dried yeast is separated and collected Set point pump=flow-rate selector of the feeding pump of the yeast suspension in the nebulization chamber (3=low, 4=medium, 5=high)

T in (° C.)=temperature of the nitrogen at the inlet of the nebulization chamber, therefore before introduction of the suspension to be nebulized T out (° C.)=temperature of the nebulization chamber after the introduction of the yeast suspension f Weight (g)=quantity of dried yeasts collected in the cyclone situated after the nebulization chamber Estimate recovery (%)=weight of yeasts collected in the cyclone with respect to the quantity of yeasts fed in suspension.

The yeasts collected in the cyclone positioned after the nebulization chamber prove to be dried, as they have a residual water content of less than 5%. These dried yeasts were characterized by means of thermogravimetric analyses. Thermogravimetry consists of a registration of the evolution of the weight in air between room temperature and 930° C., with a gradient of 10° C./min. The samples subjected to thermogravimetry are those listed in Table 2 below.

TABLE 2

| THERMOGRAVIMETRY | |
|---|---|
| SD100 | |
| SD101 | |
| SD102 | |
| SD103 | |
| SD104 | |
| Ex 105° C. in oven | |
| SOX104 | Residue from SD100 extracted with solvent hexane |
| SOX105 | Residue from SD101 extracted with solvent ethanol |
| SOX107 | Residue from SD102 extracted with solvent ethanol |
| SOX109 | Residue from SD103 extracted with solvent ethyl acetate |
| SOX110 | Residue from SD103 extracted with solvent ethanol |
| SOX111 | Residue from SD104 extracted with solvent ethyl acetate |
| SOX112 | Residue from SD104 extracted with solvent ethanol |

The normal nebulization operation of the present instrument used as spray dryer up to a temperature of 95° C., produces an effective drying of the suspension of these yeasts (the residual water in the solids is less than 5%) but is not effective in contemporaneously effecting a the lysis of the cell membrane. Only starting from a higher temperature, in which the sample remains for about 10-20 sec. at T higher than or equal to 120° C., was a significant yield obtained in terms of extract percentage, in the following extraction process effected in the Soxhlet unit, which progressively increases with an increase in the nebulization temperature.

In short, a direct and unequivocal correlation is evident between the increase in the nebulization temperature and the effective lysis of the microorganism. During the verification tests of the lipids extracted, it was in fact demonstrated that the lysing effect increases with an increase in the temperature of the nebulization process, due to the temperature value and rapidity of the temperature increase in the sprayer, which causes breakage of the sample membrane.

FIG. 1 indicates the extraction yield (dw %) of the lipids, in relation to the nebulization temperature of the suspensions of *Lypomyces* (L), *Rhodotorula* (R) and *Cryptococcus* (C) yeasts.

As can be observed in FIG. 1, the extraction yield percentage, with the same solvent used, increases with an increase in the nebulization temperature of the microorganisms.

FIG. 2 shows the thermograms which indicate the results obtained with the method of the invention.

In particular, FIG. 2 shows a comparison between thermograms of *Lypomyces* yeast cells after nebulization at increasing nebulization temperatures, i.e. at 95° C., 130° C. and 150° C., but before solvent extraction of the lipids contained therein.

The thermograms of FIG. 2 represent the residual weight % curves (left scale) and derivative curves (D %/DT) obtained by heating the nebulized samples in an atmosphere of air with a heating profile of 10° C./min at temperatures of 95° C., 130° C. and 150° C.

The temperature at which the main weight loss is observed in the thermogram, is within the range of 280-380° C. This weight loss indicates the breakage of the membrane and is correlated, in the graph, with the temperature at which the sample has been nebulized. In particular, it can be observed from this comparison that a higher nebulization temperature of the initial suspensions (as indicated in Table 1, the sample SD100 was nebulized at 95° C. (T out=95° C.), the sample SD101 at 130° C. and the sample SD102 at 150° C.) leads to a lower temperature with respect to the weight loss (breakage of the membrane) of the sample analyzed.

For comparative purposes, FIG. 3 shows the thermogram of a suspension of *Lypomyces* yeast dried in an oven at 105° C., from which it can be deduced that the weight loss, i.e. the measurement of a hypothetical lysis due to the thermal drying effect alone, does not take place at these temperatures which are those normally used in the drying technology of a spray-dryer. Only with much higher temperatures, and longer treatment times by a few orders of magnitude with respect to approximately ten microseconds, can the thermal lysis lead to breakage of the membranes of the yeast used in the example of nebulising. The thermograms of FIG. 2 also show how the residual humidity content in the samples produced with nebulization was lower than 5% (weight loss at a temperature of 105° C., less than 5%) and how there was a modest ash content, less than 4% (residual weight at a temperature of 600° C.). The beginning of the significant degradation phenomena is indicated by the weight loss which is observed at about 220° C.

The weight loss between 280° C. and 380° C. begins at lower temperatures with an increase in the nebulization temperature of the sample, which indicates a greater facility in releasing the endocellular substances towards the outside environment. The other weight losses observed, in particular at about 250° C., 420° C. and 500° C., which are other cell components, such as for example, carbohydrates, did not seem to be influenced, on the contrary, by the nebulization treatment to which the sample was subjected.

FIG. 4 shows the curve of the IR spectrum of the extract SOX107 (at 150° C.) (FIG. 4*b*) (again with reference to the samples indicated in Tables 1 and 2), and for direct comparison, the IR spectrum of a reference triglyceride, i.e. with triolein (FIG. 4*a*). From a comparison, it can be deduced that the spectra obtained with the method of the invention are those of triglycerides, with the band characteristic of carbonyl at 1750 $cm^{-1}$. There is also the presence of free fatty acids (band at 1705 $cm^{-1}$) deriving from the hydrolysis of the lipids (triglycerides).

Example 2

A plant scheme is illustrated below for the use of the method of the invention, wherein the lipids contained in a yeast of the *Rhodotorula* family, were extracted.

In the present example, the substance to be lysed, in suspension in the fermentation water, is treated in lysis together with n-hexane as solvent, necessary for the extraction of the lipids from the solid.

FIG. 5 represents the plant scheme of a closed-cycle solution wherein the nebulization is obtained with a usual industrial spray-dryer, in which the specifications of the operations are in line with the data listed in Example 1 and vary according to the product to be lysed, in relation to the temperature conditions and solvent used. A wide range of nebulization chambers and injection systems in line with the specific spray-drying technology are available in the catalogue.

Table 3 below provides a key of the symbols of the plant scheme of FIG. 5:

TABLE 3

| | |
|---|---|
| E-100 E-101 | Tube-bundle heat exchangers |
| q100 | Energy supplied for the heating by means of an external service fluid |
| VLV-100 | Lamination valve |
| MIX-101 | Sprayer or nebulizer |
| V-100 | Nebulization chamber |
| E-102 | Heat exchanger with wall vapour of V-100 |
| C-500-2 | Column for water-solvent separation |
| X-100 | Oil-solid lipid separator |
| MIX-102 | Filling process of the solvent |
| P-100 | Solvent entrainment pump |
| RCY-2 | Recycling |

Figure 1:
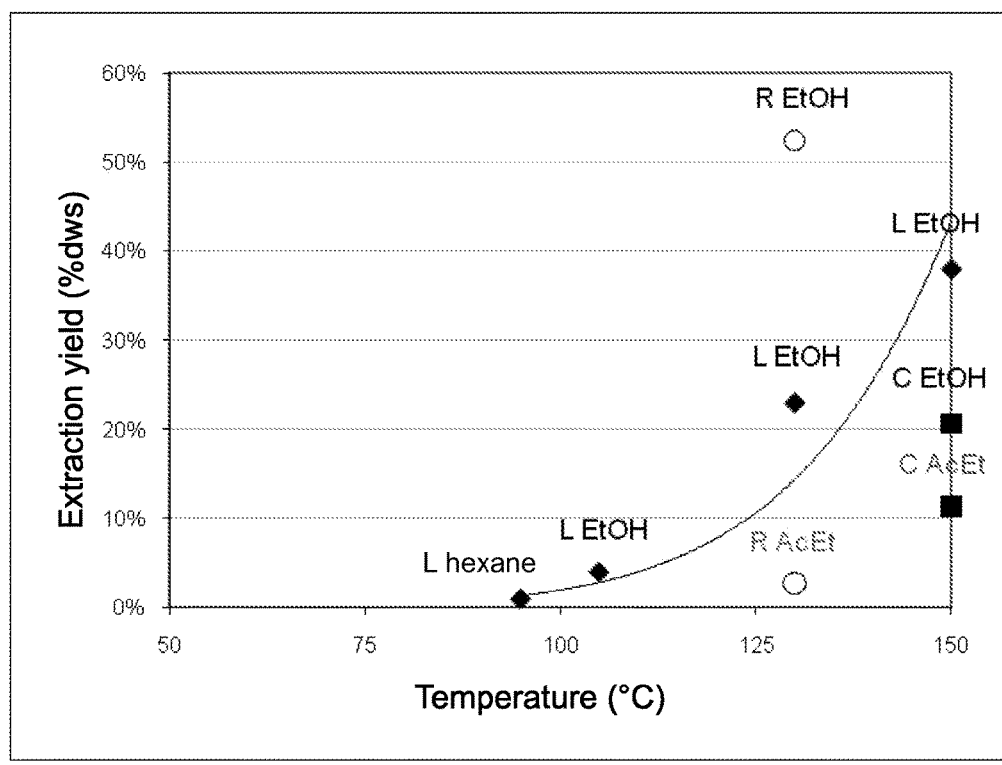
FIG. 1 shows the extraction yield (dw %) of the lipids with respect to the dry weight, in relation to the nebulization temperature of the suspensions of the yeasts *Lypomyces* (L), *Rhodotorula* (R) and *Cryptococcus* (C).
Figure 2:
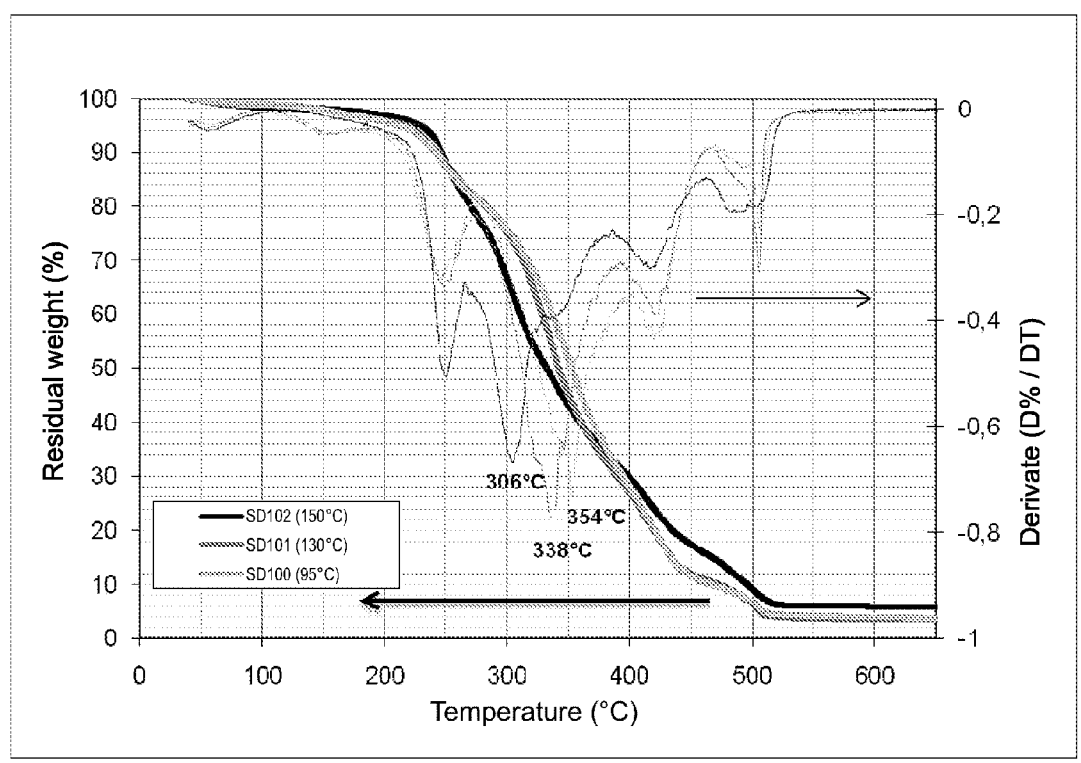
FIG. 2 shows the comparison between thermograms of *Lypomyces* yeast cells after nebulization but before solvent extraction of the lipids contained therein, at increasing nebulization temperatures.
Figure 3:
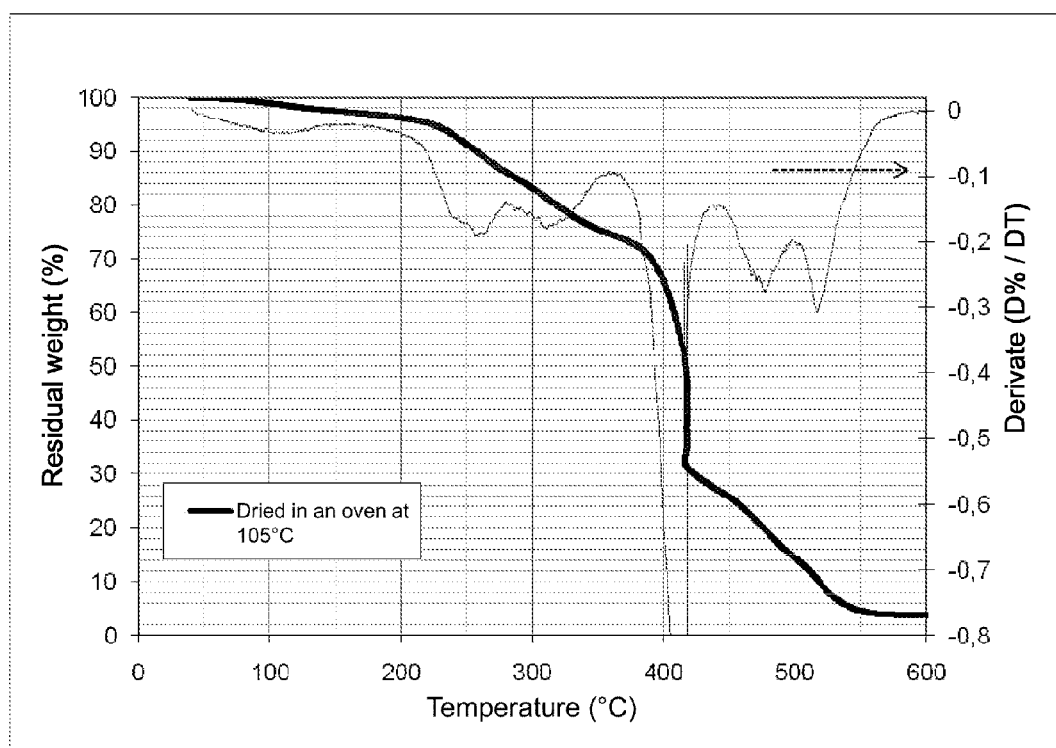
FIG. 3 shows the thermogram of *Lypomyces* yeast cells dried in an oven at 105° C.; the residual weight % curve (left scale) and derivative curves (D %/DT) can be observed.
Figure 4:
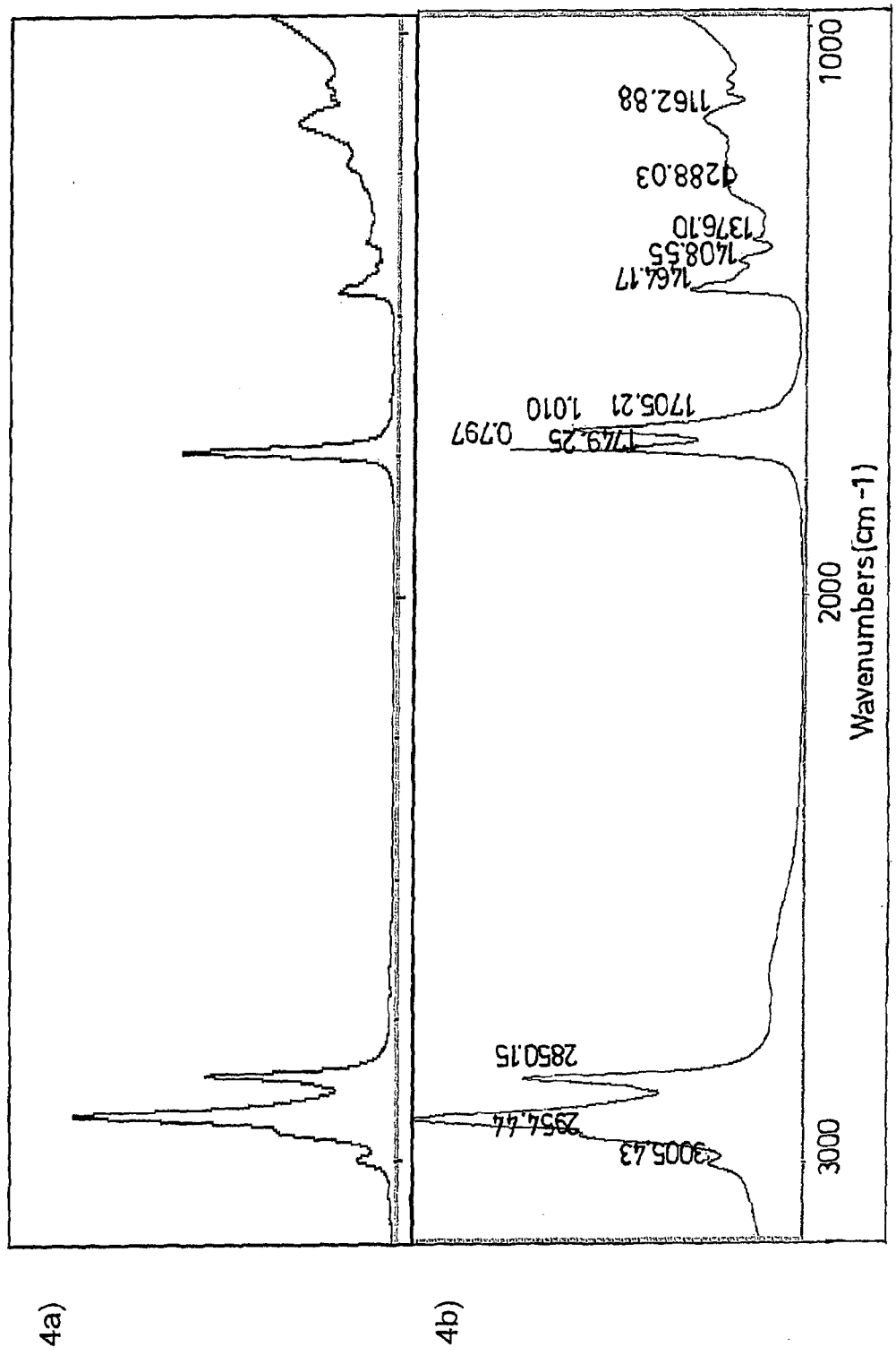
FIG. 4 shows the IR spectrum of triolein (FIG. 4a) and the extract SOX107 (at 150° C.) (FIG. 4b).
Figure 5:
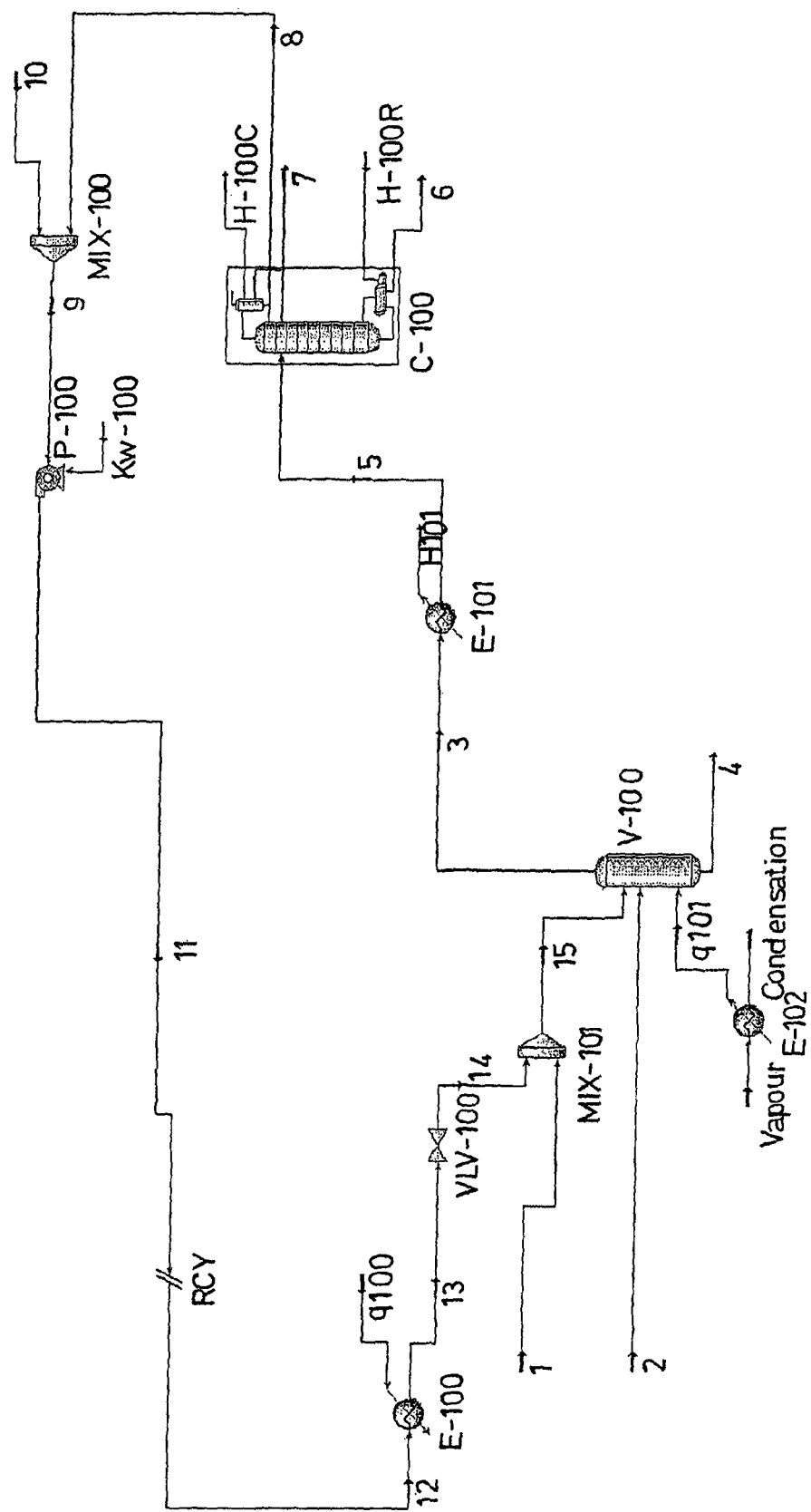
FIG. 5.

The scheme represented in FIG. 5 is composed of a pump P-100 which carries a solvent for the extraction of the intracellular product, under pressure at an adequate value for the heat exchange and lysing operation in the nebulization chamber. Here, a specific temperature for the cell disruption of the microorganism and a residence time of the nebulized suspension within the range of 5-300 sec, preferably about 10 seconds, must be obtained.

The liquid (flow "12") passes through an exchanger without changing phase, and then enters a static grid mixer where it encounters and entrains the suspension or turbid solution to be lysed (flow "1") to a spray-dryer (nebulizer).

The turbulent radial mixing mechanism in the mixer reduces the radial velocities and dimensions of the monophase aggregates to be mixed, increasing the contact surface and stimulating the thermal and chemical concentration exchange, improving the mixing. The length of the dispersers necessary depends on the contact time required. For mass transfer processes in which the equilibrium is rapidly established, a length of 5 diameters is generally sufficient.

There is a vast state in the art on various types of pneumatic nebulizers for applications that can be used according to the concentration and/or viscosity characteristics of the feeding. The following can be mentioned, for example:

Concentric tube nebulizers
Cross flow nebulizers
DIN (Direct Injection Nebulizer)
Perforated disc nebulizers
Babington nebulizers in the "V-groove" and "cone-spray" versions
"Parallel Path" nebulizers.

In industrial systems, the nebulization of the products is effected with various spray-dryers, under controlled temperature and air-flow conditions, which can be rotating for an improved homogenization of the chamber V-100.

The liquid, or liquefied gas for the operating conditions, introduced into the mixer, exits from a nozzle and is dispersed by a diffuser in the form of aerosol. The suspension is divided into nebulized drops which then come into contact with water vapour in the present example for the temperature control of the nebulization chamber V-100 and expands. The temperature of this chamber is kept above the lysis threshold by a flow of additional and wall vapour.

The evaporation of part or all of the liquid solvent and water which accompanies the product to be lysed, releases the cells in a suspension of high-boiling oils (as already indicated, lipids have a normal boiling point higher than 300° C.).

The vapours evacuate the chamber V-100 under controlled temperature and flow conditions. The suspension of solid residues and lipids is continuously discharged, by gravity and pressure, from the nebulization chamber, and can be sent to separation of the cell residues (this is the flow indicated with "4" in the scheme in FIG. 5). The flow "2" represents a flow of water vapour for the temperature control of the nebulization chamber.

After cooling to below 100° C., the vapours are sent to a recovery column of the solvent, C-100, which is then recycled together with a make-up flow to the pump P-100.

The water separated (streams "6" and "7") is sent to a treatment plant before being disposed of.

Table 4 provided in FIG. 6, indicates the material and energy balance of the example relating to a *Rhodotorula* treated via sugar fermentation.

The scheme was developed for a concentration of solids to be lysed at 30% by weight in the turbid solution to be treated. The specification conditions for the lysing operation are indicated in Table 4. In this respect, 1.52 kg of vapour are necessary at 30 bar and 21 kg of cooling water per kg of turbid solution to be lysed. The other exchanges are compensated internally.

The extraction operation is then effected on a tricanter using hexane.

If the feeding, resulting from a filtration, related to a turbid solution at 70% by weight of microorganisms, the characteristic consumptions would drop to an extremely convenient 0.37 kg of Vapour and 4.25 kg of tower water per kg of turbid solution to be lysed.

The invention claimed is:

1. A method for recovering one or more intracellular components from a suspension comprising one or more microorganisms, the method comprising:
    co-feeding at least two streams to a nebulizer, wherein a first stream comprises an aqueous suspension comprising one or more microorganisms to be lysed and a second stream comprises a liquid or gaseous solvent;
    nebulizing said suspension in a nebulization chamber maintained at a temperature ranging from 120° C. to 180° C., thereby lysing one or more cell walls of the one or more microorganisms to form a suspension comprising the one or more intracellular components and one or more cell residues derived from the lysing, and a vapour phase comprising the liquid or gaseous solvent; and
    separating the one or more intracellular components from the one or more cell residues.

2. The method of claim 1, wherein the liquid or gaseous solvent is a polar organic solvent.

3. The method of claim 2, wherein the polar organic solvent is at least one selected from the group consisting of an alcohol, an ester, and a ketone.

4. The method of claim 1, wherein the liquid or gaseous solvent is an apolar organic solvent.

5. The method of claim 4, wherein the apolar organic solvent is at least one selected from the group consisting of an alkane and a mixture of various organic refinery substances.

6. The method of claim 1, wherein the the nebulizing comprises nebulizing the suspension in a nebulization chamber containing an inert gas.

7. The method of claim 1, wherein the temperature of the nebulization chamber ranges from 120° C. to 160° C.

8. The method of claim 1, wherein at least one of the one or more microorganisms is a yeast, an alga, a bacterium, and a mildew or a combination thereof.

9. The method of claim 8, wherein the at least one of the one or more microorganisms is the yeast.

10. The method of claim 1, wherein the one or more intracellular components are one or more intracellular lipids produced by the one or more microorganisms following sugar fermentation.

11. The method of claim 1, wherein the the separating comprises separating gravimetrically or by centrifugation.

12. The method of claim 1, wherein the suspension comprising the one or more intracellular components and one or more cell residues is subjected to at least one additional lysing operation by recycling the same suspension.

13. The method of claim 12, wherein the recycling of the suspension comprising the one or more intracellular components and one or more cell residues is carried out with an initial suspension to be lysed, upstream of the nebulization chamber.

14. The method of claim 12, wherein the recycling of the suspension comprising the one or more intracellular components and one or more cell residues is carried out towards a lysing unit downstream of the nebulization chamber.

15. The method of claim 1, wherein the liquid or gaseous solvent is an organic solvent.

16. The method of claim 2, wherein the polar organic solvent is at least one selected from the group consisting of methanol, ethanol, isopropanol and ethyl acetate.

17. The method of claim 5, wherein the apolar organic solvent is the alkane and the alkane is at least one selected from the group consisting of hexane and iso-octane.

18. The method of claim 5, wherein the apolar organic solvent is the mixture of various organic refinery substances and one of the organic refinery substances is at least one selected from the group consisting of petroleum ether, a naphtha and an alkylated Gasoline.

19. The method of claim 6, wherein the inert gas is water vapour, carbon dioxide or a nebulization solvent in gaseous phase.

20. The method of claim 9, wherein the yeast is of a genus selected from the group consisting of *Lypomyces, Rhodotorula* and *Cryptococcus*.

* * * * *